United States Patent

Fung et al.

[11] Patent Number: 5,977,133
[45] Date of Patent: Nov. 2, 1999

[54] PYRIDONE ANTIBIOTIC WITH IMPROVED SAFETY PROFILE

[75] Inventors: Anthony Fung, Gurnee; Yoek-Lin Armiger, Round Lake Park; Yat Sun Or, Libertyville, all of Ill.

[73] Assignee: Abbott Laboratories, Abbott Park, Ill.

[21] Appl. No.: 09/137,131

[22] Filed: Aug. 19, 1998

[51] Int. Cl.$^6$ .......................... A61K 31/44; C07D 471/02
[52] U.S. Cl. ............................................. 514/306; 546/138
[58] Field of Search ............................... 546/138; 514/306

[56] References Cited

U.S. PATENT DOCUMENTS 5,599,816   2/1997   Chu et al. ................................. 514/254

OTHER PUBLICATIONS

Sinkula, "Prodrug Approach in Drug Design," Medicinal Chemistry, vol. 10, pp. 306–315, 1975.

Primary Examiner—Mukund J. Shah
Assistant Examiner—Ann M. Kessinger
Attorney, Agent, or Firm—Mona Anand

[57] ABSTRACT

Antibacterial compounds having the formula

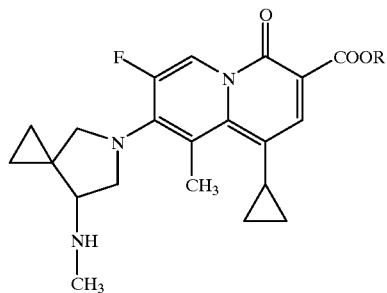

(I)

and the pharmaceutically acceptable salts, esters and amides thereof, as well as pharmaceutical compositions containing such compounds and the use of the same in the treatment of bacterial infections.

6 Claims, No Drawings

PYRIDONE ANTIBIOTIC WITH IMPROVED SAFETY PROFILE

TECHNICAL FIELD

The present invention relates to 8-(7-N-methyl-5-azaspiro[2.4]heptan-5-yl)-1 cyclopropyl-7-fluoro-4H-9-methyl-4-oxo-quinolizine-3-carboxylic acid and its pharmaceutical salts having antimicrobial activity, pharmaceutical compositions containing the compounds, methods of treatment utilizing the compounds, and processes for the chemical synthesis.

BACKGROUND OF THE INVENTION

There is a continuing need for new antibacterial agents. Although many compounds are known which are useful in the treatment of Gram-positive and Gram-negative bacterial infections as well as other microbial infections, the widespread use of such compounds continues to give rise to resistant strains of microorganisms, i.e., strains of microorganisms against which a particular antibiotic or group of antibiotics, which was previously effective, is no longer useful. Also, known antibiotics may be effective against only certain strains of microorganisms or have limited activity against either Gram-positive or Gram-negative, aerobic or anaerobic organisms.

The therapeutic use of certain quinolizinone derivatives has been described previously. For example, Y. Kitaura et al., in U.S. Pat. No. 4,650,804, issued Mar. 17, 1987, have disclosed quinolizinone compounds having a tetrazolylcarbamoyl substituent which are useful for the treatment of allergic and ulcer diseases. J. V. Heck and E. D. Thorsett, in European Patent Application No. 0308019, published Mar. 22, 1989, have disclosed the use of certain 4-oxo-4H-quinolizine-3-carboxylic acids and derivatives thereof for treating bacterial infections. U.S. Pat. Nos. 5,726,182; 5,599,816; and 5,580,872 disclose certain quinolinzinone type compounds and derivatives thereof for antibacterial activity. However, some of the compounds disclosed therein may not have desirable in vivo safety profile and pharmacokinetics. Therefore, there remains an ongoing need for novel compounds which have improved antimicrobial potency, saftey and/or different spectra of activity.

SUMMARY OF THE INVENTION

In one aspect, the present invention relates to a compound represented by the following structural formula (I):

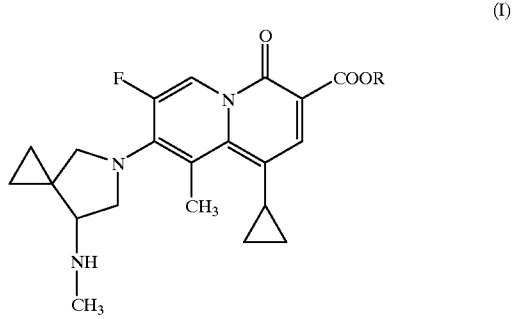

(I)

as well as the pharmaceutically acceptable salts, esters and amides thereof. In the above formula, R is selected from the group consisting of hydrogen, loweralkyl, a pharmaceutically acceptable cation, and a prodrug ester group.

The above compounds of the invention are found to have surprisingly superior antibacterial activity against broad spectrum antibacterial activity. Specifically, the compounds exhibit superior antibacterial activity against aerobic, anaerobic and fastidious pathogens of the genera Staphylococcus, Streptococcus, and enteriococci. The compounds of the invention are found to exhibit safer in vivo profile than the compounds disclosed in the U.S. Pat. Nos. 5,726,182; 5,599,816; and 5,580,872. It is therefore expected that the compounds of the present invention will be useful in the treatment and prevention of susceptible bacterial infections in both humans and lower animals. In addition, the compounds may be used in scrub solutions for surface inhibition of bacterial growth.

Accordingly, in a further aspect of the present invention are disclosed pharmaceutical compositions which are useful in the treatment and prophylaxis of bacterial and/or fungal infection in humans and animals, comprising a compound of the invention in combination with a pharmaceutically acceptable carrier.

In yet another aspect of the present invention is disclosed a method of treating and/or preventing microbial infections in human or animal patients in need of such treatment, comprising the administration to such patients of a therapeutically effective amount of a compound of the invention in amounts and for such a period of time as are sufficient to produce the desired result.

DETAILED DESCRIPTION OF THE INVENTION

The term "pharmaceutically acceptable cation" refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylammonium, tetraalkylammonium, diethanolammmonium, triethanolammonium, and guanidinium ions, and protonated forms of lysine, procaine and choline. Cations may be interchanged by methods known in the art, such as ion exchange. Where compounds of the present invention are prepared in the carboxylic acid form (that is, where R is hydrogen) addition of a base form of the cation, (such as a hydroxide or a free amine) will yield the appropriate cationic form.

By "pharmaceutically acceptable salts, esters and amides", as of the compounds of formula I, is meant those carboxylate salts, amino acid addition salts, esters and amides which are, within the scope of sound medical judgement, suitable for use in contact with the tissues of humans and lower animals without undue toxicity, irritation, allergic response and the like, commensurate with a reasonable benefit/risk ratio, and effective for their intended use, as well as the zwitterionic forms thereof.

Pharmaceutically acceptable salts are well known in the art. For example, S. M Berge et al. describe pharmaceutically acceptable salts in detail in *J. Pharmaceutical Sciences*, 66:1–19 (1977). Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate and the like or metal salts such as sodium, potassium, magnesium or calcium salts or amino salts such as ammonium, triethylamine salts and the like, all of which may be prepared according to conventional methods.

Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I may be prepared according to conventional methods.

Examples of pharmaceutically acceptable, non-toxic amides of the present invention include amides derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I may be prepared according to conventional methods. It is intended that amides of the present invention include amino acid and peptide derivatives of the compounds of formula I as well.

As used herein, the term "pharmaceutically acceptable carrier" means a non-toxic, inert solid, semi-solid or liquid filler, diluent, encapsulating material or formulation auxiliary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, and preservatives can also be present in the composition, according to the judgement of the formulator.

The term "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14–21 of "Bioreversible Carriers in Drug Design: Theory and Application", edited by E. B. Roche, Pergamon Press:New York (1987). It is intended that these references, and any others cited throughout this specification, are incorporated herein by reference.

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in the book "Pro-drugs as Novel Delivery Systems", by Higuchi and Stella, cited above.

The term "protecting group" is well-known in the art and refers to substituents on functional groups of compounds undergoing chemical transformation which prevent undesired reactions and degradations during a synthesis; see, for example, T. H. Greene, "Protective Groups in Organic Synthesis", John Wiley & Sons, New York (1981).

The preferred compounds of the invention are those having the formula:

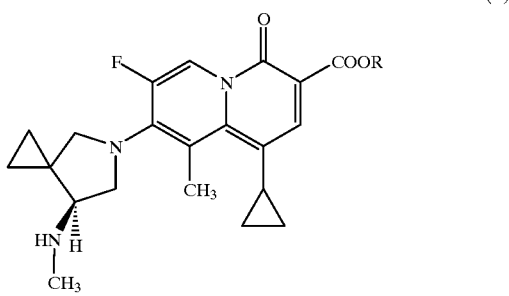

(II)

wherein R is as defined above.

According to the methods of treatment of the present invention, the compounds of the invention may be administered alone or in combination or in concurrent therapy with other agents. When utilizing the compounds of the present invention for antimicrobial therapy, the specific therapeutically effective dose level for any particular patient will depend upon a variety of factors including the disorder being treated and the severity of the disorder; activity of the particular compound used; the specific composition employed; the age, body weight, general health, sex and diet of the patient; the time of administration, route of administration, and rate of excretion of the specific compound employed; the duration of the treatment; drugs used in combination or coincidently with the specific compound employed; and like factors well known in the medical arts.

The total daily dose of the compounds of this invention administered to a host in single or in divided doses can be in amounts, as for example from 0.1 to 200 mg/kg body weight or more usually from 0.25 to 100 mg/kg body weight. Single dose compositions may contain such amounts or submultiples thereof as make up the daily dose.

According to the pharmaceutical compositions of the present invention, the compounds of the invention may be administered orally, parenterally, by inhalation spray, rectally, or topically in unit dosage formulations containing conventional nontoxic pharmaceutically acceptable carriers, adjuvants, diluents and/or vehicles as desired. The term "parenteral" as used herein includes subcutaneous injections, intravenous, intramuscular, intrastemal injection or infusion techniques.

Injectable preparations, as for example sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, as for example as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of a drug from subcutaneous or intramuscular injection. The most common way to accomplish this is to inject a suspension of crystalline or amorphous material with poor water solubility The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. Depot injectables can also be made by entrapping the drug in liposomes or microemulsions which are compatible with body tissues.

Suppositories for rectal or vaginal administration of the drug can be prepared by mixing the drug with a suitable nonirritating excipient such as cocoa butter and polyethylene glycol which are solid at ordinary temperature but will melt in the rectum or in the vagina and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsifying and suspending agents; and sweetening, flavoring and perfuming agents.

If desired, the compounds of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use.

The active compounds can also be in micro-encapsulated form with one or more excipients as noted above.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons or substitutes therefor.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

A further possibility for delivery and/or utilization of the compounds of the present invention is by chemical conjugation of the compounds with other antibacterials such as beta-lactams. Similar dual-action conjugates (between beta-lactams and quinolones) are proposed in the published European patent application No. 597 303 of Dax et al. (published on May 18, 1994) and the published international patent application No. PCT/US92/08246 of White et al. (Publication No. WO 93/07154, published on Apr. 15, 1993). In the manner suggested by these references, a carbon-nitrogen bond or other covalent link may be formed between, for example, either an amino substituent at the C-8 position or a carboxylic acid group at the C-3 position of a compound of the present invention, and an alkyl or other group of a beta-lactam.

The compounds are prepared as shown in Scheme 1:

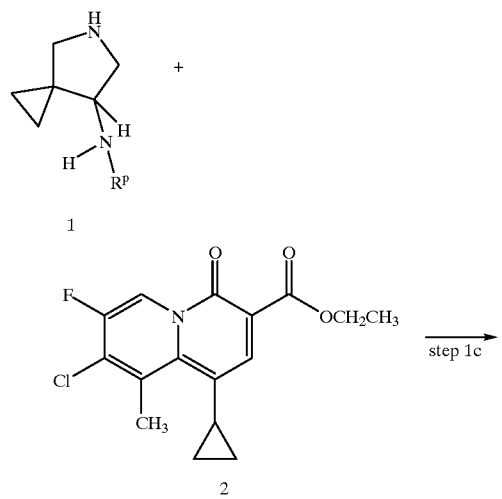

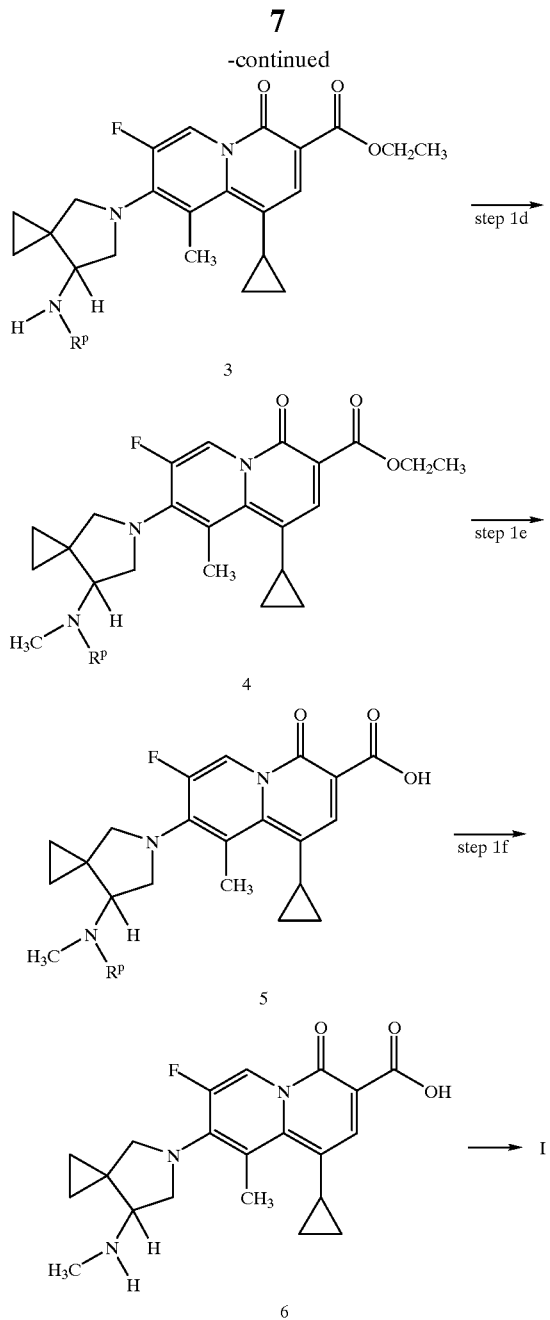

As shown in Scheme 1, 8-chloro- 1-cyclopropyl-7-fluoro-9-methyl-4-oxo-4H- quinolizine-3-carboxylic acid ethyl ester (compound 2) is reacted with 7-amino-5- azaspiro[2.4] heptane (compound 1) in the presence of a non-nucleophilic base such as triethylamine, diisopropylethylamine, or pyridine, preferably triethylamine. The reaction proceeds by nucleophilic displacement of the chloro group of compound 2 to afford compound 3 (step 1c). In compound 1, $R^P$ represents a nitrogen protecting group. Commonly used nitrogen-protecting groups are disclosed in Greene, "Protective Groups In Organic Synthesis," John Wiley & Sons, New York (1981), hereby incorporated by reference. Selective protection and deprotection of the nitrogen group depend on the nature of $R^P$ and may be carried out by methods known in the art and as described in Greene, supra.

Methylation of compound 3 with $CH_3$-X, wherein X is a leaving group such as a halide or sulfonate in the presence of a base such as an alkali metal hydride or bis (trimethylsilylamide), preferably sodium bis (trimethylsilylamide) affords compound 4 (step 1d). Hydrolysis of compound 4 with an alkali metal hydroxide such as lithium, sodium, or potassium hydroxide provides carboxylic acid compound 5 (step 1e). Deprotection of the protecting group $R^P$ of compound 5 (step 1f) is accomplished by reaction with strong acid such as HCl or HBr in acetic acid or dioxane, preferably HCl in dioxane to afford compound. Compound 6 may be converted into a pharmaceutically acceptable salts, esters and amides thereof by the methods known in the art to obtain compound of formula I.

The foregoing may be better understood from the following examples, which are presented for the purpose of illustration and are not intended as a limitation upon the scope of the invention.

EXAMPLE 1

1-cyclopropyl-8-(7(S)-N-methylamino-5-azaspiro [2.4]heptyl)-7-fluoro-9-methyl-4-oxo-4H-guinolizine-3-carboxylic acid hydrochloride Step 1a: 8-chloro- 1 -cyclopropyl-7-fluoro-9-methyl-4-oxo-4H-guinolizine-3-carboxylic acid ethyl ester (Compound 2, Scheme 1)

The title compound was prepared as described in Steps (a) through (i) in 253 of U.S. Pat. No. 5,599,816, incorporated herein by reference and described below.

To 250 mL of a THF solution containing 106 g (0.571 mmol) of a mixture of 4-chloro-tetrafluoropyridine and 3-chloro-tetrahydropyridine (approx 70:30 ratio, from Aldrich Chemical Co.) at −78° C. was added a solution of 38.3 g (0.399 mmol) of sodium t-butoxide in 350 mL of THF, and the solution was stirred for 2 hours at −78° C. and at ambient temperature for 16 hours. The mixture was poured into 500 mL of hexane, and this mixture was filtered through celite and the filtrate concentrated. The residue was purified by flash chromatography, eluting first with hexane, then ethyl acetate:hexane (1:4), to separate 4-t-butoxy-3-chloro-2,5,6-trifluoropyridine from the mixture of products. MS 238, 240 $(M+H)^+$; 1H NMR $(CDCl_3)\delta$:1.52 (d, J=2 Hz); $^{19}F$ NMR $(CDCl_3$, $CFCl_3$ as reference)∂: 73.75 (dd, $J_1$=14.2, $J_2$=23.2 Hz), 89.71 (dd, $J_1$=14.2, $J_2$=21.98 Hz); 152.42 (apparent t, J=22 Hz).

To 4-t-butoxy-3-chloro-2,5,6-trifluoropyridine (24.92 g, 0.104 mmol) in 100 mL of methanol was added 2.5 g of Pearlman's catalyst (Aldrich Chemical Co.), and the mixture was stirred at ambient temperature for 14 hours under and atmosphere of hydrogen. An additional 2.5 g of catalyst was added, and the mixture was stirred for another 22 hours. The mixture was filtered, the filtrate was concentrated, and the residue was extracted with hexane/ether. After filtration, the solvent was removed by evaporation, and the residue was purified by flash chromatography (ethyl acetate:hexane 1:16) to yield 12.05 g of 4-t-butoxy-2,3,6-trifluoropyridine. MS 206 $(M+H)^+$, 233 $(M+18)^+$; 1H NMR $(CDCl_3)$∂: 1.52 (s, 9H), 6.5 (m, 1H), $^{19}F$ NMR $(CDCl_3$, $CFCl_3$ as reference)∂: 72.60 (dd, $J_1$=14.3, $J_2$=21.0 Hz), 89.74 (dd, $J_1$=14.3, $J_2$=21.0 Hz), 164.68 (dt, $J_1$=4.2, $J_2$=21.0 Hz).

A freshly prepared solution of lithium diethylamide (LDA) (58.21 mmol) in 30 mL of THF at −78° C. was added to 10.0 g (48.74 mmol) of 4-t-butoxy-2,3,6-trifluoropyridine in 50 mL of THF at −78° C, and the reaction was stirred for 50 min. To the reaction mixture was added 4.3 mL (69.07 mmol) of methyl iodide, and the mixture was stirred at −78° C. for 1 hour and stirred at ambient temperature for 16 hours. The reaction was quenched with saturated $NH_4Cl$ solution, extracted with hexane, and the extracts washed with water, dried over MgSO$_4$ and concentrated to give 4-t-butoxy-2,3,6-trifluoro-5-methylpyridine as a pale yellow oil, which was taken directly to the next step. MS (220) (M+H)$^+$; 1H NMR (CDCl$_3$)∂: 1.47 (m, 9H), 2.12 (m, 3H). $^{19}$F NMR (CDCl$_3$, CFCl$_3$ as reference)∂: 75.91 (dd apparent, J$_1$=15.0, J$_2$=22.1 Hz), 93.17 (dd apparent, J$_1$=15.0, J$_2$=22.1 Hz), 156.54 (m).

A sample of 4-t-butoxy-2,3,6-trifluoro-5-methylpyridine (48.74 mmol) and 13.5 mL of hydrazine monohydrate were dissolved in 150 mL of n-propanol. The reaction was stirred at reflux temperature under nitrogen for 4 hours. The volatiles were removed, and the residue was dissolved in methylene chloride, which was washed with water and dried over MgSO$_4$. The solvent was removed to give the intermediate hydrazine product as a yellow liquid, which was dissolved in 110 mnL of methanol. To this was added 20 mL of 20% NaOH and air was passed through the solution for 16 hours. The solvents were removed at 30° C. under vacuum. The residue was dissolved in methylene chloride, which was washed with water and dried over MgSO$_4$. The solvent was removed and the crude product purified by flash chromatography, eluting with ethyl acetate:hexane 1:16 to give 4t-butoxy-2,5-difluoro-3-methylpyridine as a colorless liquid after removal of the solvents. MS (202) (M+H)$_+$; 1H NMR (CDCl$_3$)∂: 1.43 (d, 9H, J=1.5 Hz), 2.18 (d, 3H, J=1.5 Hz), 7.85 (br s, 1H); $^{19}$F NMR (CDCl$_3$, CFCl$_3$ as reference) δ: 73.37 (d, J=24.5 Hz), 142.17 (d, J=24.5 Hz).

A sample of 4-t-butoxy-2,5-difluoro-3-methylpyridine (40.8 mmol) was dissolved in 50 mL of THF and cooled to −78° C. To this was added a freshly prepared solution of LDA (0.103 mmol) in 50 mL of THF at −78° C,, and the reaction was stirred for 1 hour. The reaction was then stirred at 0° C. for 1 hour, quenched with saturated NH$_4$Cl solution and extracted with ether. The extracts were washed with saturated NaCl solution, dried over MgSO$_4$, and concentrated. The residue was purified by flash chromatography, eluting with 1:4 ethyl acetate:hexane, to yield 10.33 g of 2-(4-t-butoxy-5-fluoro-3-methyl-2-pyridinyl)cyclopropaneacetonitrile after removal of the solvent. MS 263 (M+H)$^+$; 1H NMR (CDCl$_3$)∂: 0.50 (m, 2H), 0.63 (m, 1H), .73 (m, 1H), 1.60 (m, 1H), 1.43 (d, 9H, J=2 Hz), 2.29 (s, 3H), 3.76 (d, 1H, J=8 Hz), 8.30 (d, 1H, J=3 Hz). IR (neat) 2240, 1580, 1470 cm$^{-1}$.

A sample of 2-(4-t-butoxy-5-fluoro-3-methyl-2-pyridinyl)cyclopropaneacetonitrile (5.21 g, 19.86 mmol) was dissolved in 50 mL of trifluoroacetic acid, the reaction was stirred under nitrogen for 1 hour at ambient temperature, and the material concentrated to dryness. The residue was dissolved in a mixture of 15.6 mL of DMF and 90 mL of methylene chloride. This solution was cooled in a water bath as 18.8 mL (19.86 mmol) of POCl$_3$ was added, then the reaction was stirred at ambient temperature for 16 hours. The reaction was quenched by pouring it into ice water, and the mixture was extracted with methylene chloride. The aqueous solution was adjusted to pH7 with NaOH and re-extracted with methylene chloride. The extracts were combined and washed with water, dried over MgSO$_4$ and concentrated. The residue was purified by flash chromatography with 1:4 ethyl acetate:hexane to give 3.26 g of 2-(4-chloro-5-fluoro-3-methyl-2-pyridinyl)cyclopropaneacetonitrile as a colorless liquid after removal of the solvents. MS 225, 227 (M+H)$^+$; 1H NMR (CDCl$_3$)∂: 0.48 (m, 1H), 0.59 (m, 1H), 0.66 (m, 1H), 0.77 (m, 1H), 1.50 (m, 1H), 2.48 (s, 3H), 3.80 (d, 1H, J=8 Hz), 8.39 (s, 1H). IR (neat) 2240, 1570, 1460 cm$^{-1}$.

A sample of 2-(4-chloro-5-fluoro-3-methyl-2-pyridinyl)cyclopropaneacetonitrile (3.26 g, 14.51 mmol) was dissolved in 10 mL of ethanol, and gaseous HCl was introduced until 4 g had been dissolved. The solution was heated to reflux, and 0.36 mL of water was added, then the mixture was stirred for 1 hour. The reaction was cooled, then poured into water, and the mixture was adjusted to pH7 with NaHCO$_3$. The mixture was then extracted with methylene chloride, which was washed with water, dried over MgSO$_4$ and concentrated. The residue was triturated with 1:4 ethyl acetate:hexane, and filtered. The filtrate was concentrated and the residue was purified by flash chromatography with 1:4 ethyl acetate:hexane to give 2.262 g of ethyl 2-(4-chloro-5-fluoro-3-methyl-2-pyridinyl)cyclopropaneacetate after removal of the solvent. MS 272, 274 (M+H)$^+$; 1H NMR (CDCl$_3$)∂: 0.12 (m, 1H), 0.38 (m, 1H), 0.53 (m, 1H), 0.76 (m, 1H), 1.20 (t, 3H, J=7 Hz), 1.67 (m, 1H), 2.40 (s, 3H), 3.23 (d, 1H, J=9 Hz), 4.16 (q, 2H, J=7 Hz), 8.36 (s, 1H).

A sample of ethyl 2-(4-chloro-5-fluoro-3-methyl-2-pyridinyl)cyclopropaneacetate (1.73 g, 6.37 mmol) was dissolved in 10 mL of THF and stirred with water bath cooling and 3.2 mmol of LiAlH$_4$ (LAH) was added. The mixture was stirred at ambient temperature for 1 hour, then poured into water. This mixture was extracted with ether, the extracts were washed, dried and concentrated to give 1.48 g of a colorless oil. This oil was dissolved in 10 mL of methylene chloride and added to a solution of 3.8 mL (7.6 mmol) of oxalyl chloride and 1.1 mL of DMSO (15.5 mmol) in 15 mL of methylene chloride stirred at −78° C. The solution was stirred for 15 min, and 4.4 mL (31.6 mmol) of triethylamine was added. The stirring was continued at −78° C. for 5 min and at −10° C. for 10 min. The reaction was quenched with water, and extracted with methylene chloride. The extract was washed, dried and concentrated to give 1.49 g of 2-(4-chloro-5-fluoro-3-methyl-2-pyridinyl)cyclopropane acetaldehyde, which was taken directly to the next step without further purification. MS 228, 230 (M+H)$^+$; 1H NMR (CDCl$_3$)∂: 0.25 (m, 1H), 0.35 (m, 1H), 0.60 (m, 1H), 0.75 (m, 1H), 1.53 (m, 1H), 2.38 (s, 3H), 3.19 (dd, 1H, J=3, J=9 Hz), 8.37 (s, 1H), 9.86 (d, 1H, J=3 Hz).

A sample of 2-(4-chloro-5-fluoro-3-methyl-2-pyridinyl)cyclopropane acetaldehyde (6.37 mmol) was dissolved in 50 mL of ethanol, and to this were added 1.5 mL of piperidine, 1.5 mL of acetic acid, and 5 mL of diethyl malonate (32.9 mmol). The reaction was heated at reflux under nitrogen for 4 hours. The solvents were then removed, and the residue was dissolved in ether. The ether was washed with water and brine, then dried over MgSO$_4$ and concentrated Purification in a kugelrohr apparatus gave 2.4 g of the crude condensation product. This intermediate product was dissolved in 20 ML of of Dowtherm A™, and this solution was added to 100 mL of Dowtherm A™ heated to 235° C. The reaction was then stirred at 220° C. for 45 min. After cooling, the product was separated from the solvent by flash chromatography, eluting with hexane to remove the solvent and then with 1:4 ethyl acetate hexane to remove the product. In this manner 1.065 g of 8-chloro-1- cyclopropyl-7-fluoro-9-methyl-4-oxo-4H-quinolizine-3-carboxylic acid ethyl ester was obtained after removal of the solvent. MS 324, 326 (M+H)$^+$; 1H NMR (CDCl$_3$)∂: 0.75 (m, 2H), 1.07 (m, 2H), 1.42 (t, 3H, J=7 Hz), 2.31 (m, 1H), 3.08 (s, 3H), 4.42 (q, 2H, J=7 Hz), 8.40 (s, 1H), 9.44 (d, 1H, J=6 Hz).

Step 1b: 7(S)-[(tert-butoxycarbonyl)amino]-5-azaspiro[2.4]heptane (Compound 1. Scheme 1)

The title compound was prepared in 10 steps from 1-acetylcyclopropanecarboxylic acid as described in *J. Med. Chem.* 1994, 37, 3344–3352 (Examples 17–27b).

Step 1c: (Compound 3, Scheme 1)

A solution of compound 2 (11 g, 51.89 mmol), compound 1, (14 g, 43.24 mmol) and triethylamine (27 mL), in DMF (65 mL) under N2 was heated for 18 hours in a 55° C. oil bath, concentrated, and dried under high vacuum to remove residual DMF. The resulting brown oil was dissolved in ethyl acetate, washed sequentially with water and brine, dried (MgSO$_4$), filtered, and concentrated. Purification of the residue on silica gel with a gradient of from 1% methanol/CH$_2$Cl$_2$ to 2–3% methanol/CH$_2$Cl$_2$ to 3% methanol/CH$_2$Cl$_2$/0.5% NH$_4$OH provided 20.2 g (94%) of compound 3.

mp 88–90 ° C.; MS (DCI/NH$_3$) m/z 500 (M+H)$^+$; $^1$H NMR (CDCl$_3$) d 0.51–1.04 (t, 3H), 1.45 (s 9H), 2.17 (m, 1H), 2.63 (s, 3H), 3.32 (d, 1H), 3.64 (m, 1H), 3.82 (bm, 1H), 4.02 (dd, 1H), 4.18 (m, 1H), 4.4 (q, 2H), 4.73 (bm, 1H), 8.21 (s, 1H), 9.27 (d, 1H); Anal. calc'd for C$_{27}$H$_{34}$N$_3$O$_5$F.0.5 H$_2$O: N, 63.76; H, 6.93; N, 8.26. Found C, 63.38; H 6.92, N, 8.86.

Step 1d (Compound 4, Scheme 1)

A solution of compound 3 (100 mg, 0.2 mmol) in THF (1 mL) at -60 ° C. (CO$_2$/chloroform) under N$_2$ was treated with a 1M solution of sodium bis(trimethylsilyl)amide in THF (0.44 mL, 0.44 mmol), stirred at –60 ° C. for 1 hour, treated with CH$_3$I (113 mg, 0.80 mmol), stirred at –60 ° C. for 30 minutes, at 0 ° C. for 30 minutes, and at room temperature for 18 hours, diluted with CH$_2$Cl$_2$, washed sequentially with 5% citric acid solution, water, and brine, and concentrated. The residue was purified on silica gel with a gradient of from 1% methanol/CH$_2$Cl$_2$ to 1% methanol/CH$_2$Cl2/0.5% NH$_4$OH to provide 30 mg of the desired product as a foamy, yellow solid and 40 mg of a mixture of unreacted staring material and compound 4. The chromatography previously described was repeated to provide an additional 25 mg of compound 4.

Step 1e (Compound 5, Scheme 1)

A solution of compound 4 (2.67 g, 0.2 mmol) and LiOH-H$_2$O (1.31 g, 31.26 mmol) in 2:1 THF/water (60 mL) was heated in an oil bath at 60 ° C. for 4 hours, cooled, diluted with CH$_2$Cl$_2$, washed with brine, dried (MgSO$_4$), filtered and concentrated. The residue was purified by column chromatography on silica gel with 1% methanol/CH$_2$Cl$_2$/0.5% acetic acid to provide 2.47 g (97%) of compound 5.

MS (DCI/NH$_3$) m/z 486 (M+H)$^+$.

Step 1f (Compound 6, Scheme 1)

A solution of compound 5 in CH$_2$Cl$_2$ was treated with 1M HCl in acetic acid (15 mL), stirred at room temperature for 2 hours, concentrated, and dried under high vacuum to 5 provide a yellow-brown solid. The solid was triturated twice with ether and once with ethanol, concentrated, and dried under high vacuum to provide 2.12 g (100%) of compound 6 as a yellow solid.

MS (DCI/NH$_3$) m/z 386 (M+H)$^+$; HRMS (DCI/NH$_3$) m/z calc'd for C$_{21}$H$_{25}$N$_3$O$_3$F: 386.1880. Found: 386.1878.

Example 2 (Not an Example of the Invention)

1 -cyclopropyl-8-(3(S)-3-amino-1 -pyrrolidinyl)-7-fluoro-9-methvl-4-oxo- 4H-quinolizine-3-carboxylic acid hydrochloride The title compound was prepared as described in Example 253 of the U.S. Pat. No. 5,599,816.

Example 3 (Not an Example of the Invention)

1-cyclopropyl-8-(3(S)-3-amino-1-pyrrolidinyl)-7-fluoro-9-methyl-4-oxo-4H- quinolizine-3-carboxylic acid hydrochloride The title compound was prepared as described above, substituting 3(R)-[(tert-butoxycarbonyl) amino]piperidine for 3(S)-[(tert-butoxycarbonyl)amino]piperidine.

Example 4 (Not an Example of the Invention)

1-cyclopropyl-8-(S,S-2,8-diaza-8-bicyclo[4.3.0] nonyl)-7-fluoro-4H-9-methyl-4-oxo-quinolizine-3-carboxylic acid hydrochloride The title compound was prepared as described in Example 320 of U.S. Pat. No. 5,599,816.

Example 5 (Not an Example of the Invention)

1-cyclopropyl-8-(7(S)-amino-5-azaspiror2.41heptvl)-7-fluoro-9-methyl4-oxo-4H-quinolizine-3-carboxylic acid hydrochloride The title compound was prepared as described in Examples 427 and 428 of U.S. Pat. No. 5,599,816.

Antibacterial activity (in-vitro MIC data)

The in vitro antibacterial activity of the compounds of the present invention was demonstrated as follows: Minimum inhibitory concentrations (MIC's) were determined by the agar dilution method, in which twelve petri dishes were prepared, each containing shifting successive aqueous 2-fold dilutions of the test compounds mixed with 10 mL of sterilized Brain Heart Infusion (BHI) agar. Each plate was inoculated with 1:100 (or 1:10 for slow-growing strains, primarily Micrococcus and Streptococcus) dilutions of up to 32 different microorganisms, using a Steers replicator block calibrated to deliver approximately 10$^4$ colony forming units (CFU's). The inoculated plates were incubated at from about 35° C. to about 37 ° C. for approximately 20–24 hours. In addition, a control plate using BHI agar containing no test compound was prepared and incubated at the beginning and at the end of each test. The quinolone antibacterial ciprofloxacin was used as a control ("Cntl").

After incubation, each petri dish was observed for the presence or absence of microorganism species growth. The numbers below the microorganism species indicate the numbers of isolates tested. The MIC's of the compound of the invention (Example 1) was compared to the MIC values of commercially available antibacterials (ciprofloxacin, trovafloxacin, sparfloxacin, and clinafloxacin) and also antibacterials known in the art (examples 2–5). The MIC is defined as the lowest concentration of test compound yielding no growth (a slight haze or sparsely isolated colonies at the inoculum spot) as compared to the growth control containing no test compound. These data are presented in Table 1.

TABLE 1

In-vitro Antibacterial Activity (MIC Data)

| Species | Number | Example | Range | MIC ($\mu$g/mL) MIC$_{50}$ | MIC$_{90}$ |
|---|---|---|---|---|---|
| S. aureus (CiproS) | 21 | 1 | 0.015–0.03 | 0.015 | 0.03 |
| | | 2 | 0.008–0.015 | 0.008 | 0.015 |
| | | 3 | 0.015–0.06 | 0 03 | 0 03 |
| | | 4 | ≦0.0005–0.002 | 0.002 | 0.002 |
| | | 5 | 0.008–0.03 | 0.015 | 0.015 |
| | | Ciprofloxacin | 0.06–0.5 | 0.25 | 0.5 |
| | | Trovafloxacin | ≦0.008–0.03 | 0.03 | 0.03 |
| | | Sparfloxacin | 0.03–0.06 | 0.03 | 0.06 |
| | | Clinafloxacin | 0.015–0.03 | 0.03 | 0.03 |
| S. aureus (CiproR) | 25 | 1 | 0.015–0.5 | 0.5 | 0.5 |
| | | 2 | 0.03–1 | 0.25 | 0.25 |

TABLE 1-continued

| Species | Number | compound | Range | MIC$_{50}$ | MIC$_{90}$ |
|---|---|---|---|---|---|
| | | 3 | 0.06–2 | 0.25 | 0.5 |
| | | 4 | 0.008–0.5 | 0.06 | 0.25 |
| | | 5 | 0.03–0.5 | 0.12 | 0.25 |
| | | Ciprofloxacin | 4→128 | 32 | 128 |
| | | Trovafloxacin | 0.25–4 | 2 | 2 |
| | | Sparfloxacin | 0.12–16 | 4 | 8 |
| | | Clinafloxacin | 0.25–2 | 0.5 | 1 |
| S. epidermidis (CiproS) | 23 | 1 | 0.015–0.03 | 0.015 | 0.03 |
| | | 3 | 0.015–0.06 | 0.03 | 0.06 |
| | | 4 | 0.015–0.03 | 0.03 | 0.03 |
| | | 5 | ≦0.004–0.03 | 0.015 | 0.03 |
| | | Ciprofloxacin | 0.06–0.5 | 0.25 | 0.25 |
| | | Trovafloxacin | 0.015–0.06 | 0.06 | 0.06 |
| | | Sparfloxacin | 0.03–0.12 | 0.06 | 0.12 |
| | | Clinafloxacin | 0.015–0.06 | 0.03 | 0.03 |
| S. epidermidis (CiproR) | 11 | 1 | 0.12–2 | 0.25 | 0.5 |
| | | 3 | 0.25–2 | 0.25 | 1 |
| | | 4 | 0.12–4 | 0.25 | 0.5 |
| | | 5 | 0.12–1 | 0.25 | 0.25 |
| | | Ciprofloxacin | 4→128 | 16 | >128 |
| | | Trovafloxacin | 1–16 | 4 | 16 |
| | | Sparfloxacin | 0.5→8 | 4 | 8 |
| | | Clinafloxacin | 0.25–2 | 0.5 | 1 |
| S. pneumoniae (PenS) | 20 | 1 | not determined | | |
| | | 2 | 0.015–0.03 | 0.03 | 0.03 |
| | | 3 | 0.06–0.12 | 0.06 | 0.12 |
| | | 4 | 0.06–0.12 | 0.06 | 0.12 |
| | | 5 | 0.03–0.06 | 0.06 | 0.06 |
| | | Ciprofloxacin | 1–8 | 2 | 4 |
| | | Trovafloxacin | 0.12–0.5 | 0.5 | 0.5 |
| | | Sparfloxacin | 0.12–0.5 | 0.25 | 0.5 |
| | | Clinafloxacin | 0.03–0.12 | 0.06 | 0.12 |
| S. pneumoniae (PenR) | 25 | 1 | 0.03–0.06 | 0.06 | 0.06 |
| | | 2 | 0.03 | 0.03 | 0.03 |
| | | 3 | 0.06–0.12 | 0.12 | 0.12 |
| | | 4 | 0.008–0.03 | 0.03 | 0.03 |
| | | 5 | 0.03–0.06 | 0.06 | 0.06 |
| | | Ciprofloxacin | 1–2 | 2 | 2 |
| | | Trovafloxacin | 0.06–0.25 | 0.25 | 0.25 |
| | | Sparfloxacin | 0.12–0.25 | 0.25 | 0.25 |
| | | Clinafloxacin | 0.06–0.25 | 0.12 | 0.25 |
| S. pneumoniae (CiproR) | 3 | 1 | not determined | | |
| | | 2 | not determined | | |
| | | 3 | 0.12–0.25 | | |
| | | 4 | 0.12–0.25 | | |
| | | 5 | 0.06–0.12 | | |
| | | Ciprofloxacin | 4–8 | | |
| | | Trovafloxacin | 0.5–1 | | |
| | | Sparfloxacin | 0.25–0.5 | | |
| | | Clinafloxacin | 0.12 | | |
| S. pyogenes | 21 | 1 | 0.03–0.06 | 0.03 | 0.06 |
| | | 3 | 0.015–0.06 | 0.03 | 0.06 |
| | | 4 | 0.03–0.06 | 0.06 | 0.06 |
| | | 5 | 0.015–0.06 | 0.03 | 0.03 |
| | | Ciprofloxacin | 0.25–4 | 0.5 | 1 |
| | | Trovafloxacin | ≦0.06–1 | 0.12 | 0.25 |
| | | Sparfloxacin | 0.12–1 | 0.25 | 0.5 |
| | | Clinafloxacin | 0.06–0.12 | 0.06 | 0.06 |
| E. faecium (CiproS) | 16 | 1 | 0.25–1 | 0.5 | 1 |
| | | 2 | 0.25–0.5 | 0.25 | 0.25 |
| | | 3 | 0.25–1 | 0.5 | 1 |
| | | 4 | 0.25–1 | 0.5 | 1 |
| | | 5 | 0.25–0.5 | 0.5 | 0.5 |
| | | Ciprofloxacin | 2–4 | 2 | 4 |
| | | Trovafloxacin | 0.25–1 | 0.5 | 1 |
| | | Sparfloxacin | 0.5–32 | 0.5 | 1 |
| | | Clinafloxacin | 0.5–8 | 1 | 2 |
| E. faecium (CiproR) | 2 | 1 | 0.5–4 | | |
| | | 2 | 0.5–2 | | |
| | | 3 | 1–4 | | |
| | | 4 | 0.5–4 | | |
| | | 5 | 0.5–4 | | |
| | | Ciprofloxacin | 64→128 | | |
| | | Trovafloxacin | 2–32 | | |
| | | Sparfloxacin | 8–32 | | |
| | | Clinafloxacin | 2–8 | | |
| E. faecium (VanS) | 11 | 1 | 0.12–1 | 0.5 | 1 |
| | | 2 | not determined | | |
| | | 3 | not determined | | |
| | | 4 | 0.12–1 | 0.5 | 1 |
| | | 5 | 0.06–0.5 | 0.25 | 0.25 |
| | | Ciprofloxacin | 1–4 | 4 | 4 |
| | | Trovafloxacin | 0.25–4 | 2 | 2 |
| | | Sparfloxacin | 1–4 | 1 | 2 |
| | | Clinafloxacin | 0.12–1 | 0.5 | 1 |
| E. faecalis (VanS) | 17 | 1 | 0.12–0.25 | 0.12 | 0.25 |
| | | 2 | 0.03–0.12 | 0.06 | 0.12 |
| | | 3 | 0.12–0.25 | 0.25 | 0.25 |
| | | 4 | 0.12–0.25 | 0.12 | 0.25 |
| | | 5 | 0.06–0.25 | 0.12 | 0.25 |
| | | Ciprofloxacin | 1–4 | 2 | 4 |
| | | Trovafloxacin | 0.25–1 | 0.5 | 1 |
| | | Sparfloxacin | 0.25–1 | 0.5 | 0.5 |
| | | Clinafloxacin | 0.12–0.25 | 0.25 | 0.25 |
| Enterococcus spp. (VanR) | 21 | 1 | 0.06–4 | 0.5 | 1 |
| | | 2 | ≦0.12–2 | 0.25 | 0.25 |
| | | 3 | 0.12–4 | 0.5 | 1 |
| | | 4 | 0.06–4 | 1 | 1 |
| | | 5 | 0.25–4 | 0.5 | 0.5 |
| | | Ciprofloxacin | 1→128 | 4 | 4 |
| | | Trovafloxacin | 0.06–32 | 1 | 1 |
| | | Sparfloxacin | 0.25–32 | 0.5 | 8 |
| | | Clinafloxacin | ≦0.12–8 | 1 | 2 |
| E. coli | 25 | 1 | 0.004–0.015 | 0.015 | 0.015 |
| | | 2 | 0.004–0.015 | 0.004 | 0.008 |
| | | 3 | 0.015–0.06 | 0.03 | 0.06 |
| | | 4 | ≦0.008 | ≦0.008 | ≦0.008 |
| | | 5 | ≦0.004–0.015 | ≦0.004 | 0.015 |
| | | Ciprofloxacin | 0.008–0.03 | 0.03 | 0.03 |
| | | Trovafloxacin | 0.015–0.03 | 0.03 | 0.03 |
| | | Sparfloxacin | 0.004–0.03 | 0.015 | 0.03 |
| | | Clinafloxacin | 0.008–0.03 | 0.015 | 0.015 |
| Salmonella spp. | 23 | 1 | 0.004–0.12 | 0.03 | 0.03 |
| | | 3 | 0.015–0.5 | 0.06 | 0.06 |
| | | 4 | 0.004–0.12 | 0.03 | 0.06 |
| | | 5 | 0.004–0.12 | 0.015 | 0.03 |
| | | Ciprofloxacin | 0.004–0.5 | 0.03 | 0.03 |
| | | Trovafloxacin | 0.03–1 | 0.06 | 0.12 |
| | | Sparfloxacin | 0.004–0.5 | 0.03 | 0.06 |
| | | Clinafloxacin | 0.004–0.25 | 0.015 | 0.03 |
| Shigella spp. | 9 | 1 | 0.002–0.15 | | |
| | | 3 | 0.008–0.03 | | |
| | | 4 | 0.004–0.015 | | |
| | | 5 | ≦0.001–0.008 | | |
| | | Ciprofloxacin | 0.008–0.015 | | |
| | | Trovafloxacin | 0.015–0.06 | | |
| | | Sparfloxacin | 0.004–0.015 | | |
| | | Clinafloxacin | 0.008–0.015 | | |
| Klebsiella spp. | 29 | 1 | 0.002–0.12 | 0.015 | 0.03 |
| | | 3 | 0.015–0.5 | 0.12 | 0.12 |
| | | 4 | 0.008–0.25 | 0.06 | 0.06 |
| | | 5 | 0.002–0.12 | 0.03 | 0.06 |
| | | Ciprofloxacin | 0.004–0.5 | 0.06 | 0.12 |
| | | Trovafloxacin | 0.015–0.5 | 0.12 | 0.25 |
| | | Sparfloxacin | 0.004–0.5 | 0.06 | 0.06 |
| | | Clinafloxacin | 0.004–0.12 | 0.03 | 0.03 |
| C. freundii | 20 | 1 | 0.015–0.25 | 0.03 | 0.25 |
| | | 3 | 0.015–0.25 | 0.06 | 0.25 |
| | | 4 | 0.015–0.25 | 0.03 | 0.25 |
| | | 5 | 0.008–0.12 | 0.015 | 0.12 |
| | | Ciprofloxacin | 0.004–0.5 | 0.015 | 0.12 |
| | | Trovafloxacin | 0.003–1 | 0.06 | 0.5 |
| | | Sparfloxacin | 0.015–1 | 0.03 | 0.5 |
| | | Clinafloxacin | 0.015–0.12 | 0.03 | 0.12 |
| P. mirabilis | 20 | 1 | 0.03–0.25 | 0.12 | 0.12 |
| | | 3 | 0.06–0.25 | 0.12 | 0.25 |
| | | 4 | 0.03–0.12 | 0.06 | 0.12 |
| | | 5 | 0.015–0.12 | 0.03 | 0.06 |
| | | Ciprofloxacin | 0.015–0.06 | 0.015 | 0.03 |
| | | Trovafloxacin | 0.25–0.5 | 0.25 | 0.5 |
| | | Sparfloxacin | 0.12–0.5 | 0.25 | 0.25 |
| | | Clinafloxacin | 0.03–0.06 | 0.03 | 0.06 |
| Providencia | 28 | 1 | 0.015–1 | 0.06 | 0.25 |

TABLE 1-continued

| | | | | |
|---|---|---|---|---|
| spp. | | 3 | 0.03–1 | 0.12 | 0.25 |
| | | 4 | 0.008–0.25 | 0.03 | 0.12 |
| | | 5 | 0.008–0.25 | 0.015 | 0.06 |
| | Ciprofloxacin | | 0.015–0.25 | 0.03 | 0.25 |
| | Trovafloxacin | | 0.03–2 | 0.25 | 2 |
| | Sparfloxacin | | 0.015–2 | 0.12 | 1 |
| | Clinafloxacin | | 0.008–0.12 | 0.015 | 0.03 |
| Enterobacter spp. | 35 | 1 | 0.008–0.12 | 0.015 | 0.03 |
| | | 3 | 0.03–0.5 | 0.06 | 0.12 |
| | | 4 | 0.015–0.12 | 0.03 | 0.12 |
| | | 5 | 0.004–0.12 | 0.015 | 0.03 |
| | Ciprofloxacin | | 0.008–0.12 | 0.015 | 0.03 |
| | Trovafloxacin | | 0.015–0.5 | 0.12 | 0.12 |
| | Sparfloxacin | | 0.008–0.25 | 0.06 | 0.06 |
| | Clinafloxacin | | 0.03–0.12 | 0.03 | 0.03 |
| P. aeruginosa (CiproS) | 24 | 1 | 0.12–4 | 0.5 | 2 |
| | | 2 | 0.015–0.5 | 0.06 | 0.25 |
| | | 3 | 0.12–1 | 0.25 | 1 |
| | | 4 | ≦0.03–2 | 0.12 | 1 |
| | | 5 | 0.06–1 | 0.12 | 1 |
| | Ciprofloxacin | | 0.06–2 | 0.12 | 0.5 |
| | Trovafloxacin | | 0.12–4 | 0.5 | 2 |
| | Sparfloxacin | | 0.06–8 | 0.5 | 1 |
| | Clinafloxacin | | 0.015–0.5 | 0.12 | 0.5 |
| P. aeruginosa (CiproR) | 20 | 1 | 4–32 | 8 | 16 |
| | | 2 | 1–4 | 2 | 2 |
| | | 3 | 16–64 | 16 | 32 |
| | | 4 | 4–64 | 8 | 16 |
| | | 5 | 4–16 | 8 | 16 |
| | Ciprofloxacin | | 32→128 | 64 | 128 |
| | Trovafloxacin | | 64→128 | >128 | >128 |
| | Sparfloxacin | | 32→128 | 64 | 128 |
| | Clinafloxacin | | 2–32 | 4 | 8 |
| B. fragilis | 18 | 1 | 0.06–0.12 | 0.06 | 0.12 |
| | | 2 | 0.06–0.5 | 0.12 | 0.5 |
| | | 3 | 0.12–0.5 | 0.25 | 0.5 |
| | | 4 | 0.12–0.5 | 0.25 | 0.25 |
| | | 5 | ≦0.015–0.06 | 0.03 | 0.03 |
| | Ciprofloxacin | | 4–32 | 8 | 16 |
| | Trovafloxacin | | 0.12–1 | 0.25 | 0.5 |
| | Sparfloxacin | | 0.5–2 | 1 | 2 |
| | Clinafloxacin | | 0.06–0.5 | 0.25 | 0.5 |
| C. difficile | 10 | 1 | 0.5 | 0.5 | 0.5 |
| | | 3 | 0.25–0.5 | 0.25 | 0.5 |
| | | 4 | 0.03–0.25 | 0.25 | 0.25 |
| | | 5 | 0.12–0.25 | 0.25 | 0.25 |
| | Ciprofloxacin | | 16 | 16 | 16 |
| | Trovafloxacin | | 1–2 | 1 | 2 |
| | Sparfloxacin | | 2–4 | 4 | 4 |
| | Clinafloxacin | | 0.12–0.25 | 0.25 | 0.25 |
| C. perfringens | 13 | 1 | 0.12–0.25 | 0.12 | 0.25 |
| | | 3 | 0.06–0.25 | 0.12 | 0.25 |
| | | 4 | 0.25–1 | 0.5 | 1 |
| | | 5 | 0.06–0.12 | 0.06 | 0.12 |
| | Ciprofloxacin | | 0.25–1 | 1 | 1 |
| | Trovafloxacin | | 0.12–0.5 | 0.25 | 0.5 |
| | Sparfloxacin | | 0.06–0.5 | 0.25 | 0.5 |
| | Clinafloxacin | | 0.06–0.12 | 0.12 | 0.12 |
| Fastidious and Miscellaneous Species | | | | | |
| H. influenzae | 18 | 1 | 0.002–0.015 | 0.004 | 0.008 |
| | | 3 | 0.008–0.06 | 0.015 | 0.03 |
| | | 4 | 0.004–0.015 | 0.015 | 0.015 |
| | | 5 | ≦0.001–0.008 | 0.002 | 0.008 |
| | Ciprofloxacin | | 0.008–0.015 | 0.015 | 0.015 |
| | Trovafloxacin | | 0.008–0.06 | 0.015 | 0.03 |
| | Sparfloxacin | | 0.004–0.03 | 0.008 | 0.015 |
| | Clinafloxacin | | 0.004–0.008 | 0.008 | 0.008 |
| M. catarrhalis | 18 | 1 | 0.008–0.03 | 0.015 | 0.03 |
| | | 3 | 0.015–0.06 | 0.06 | 0.06 |
| | | 4 | 0.015–0.03 | 0.015 | 0.03 |
| | | 5 | 0.015–0.03 | 0.015 | 0.03 |
| | Ciprofloxacin | | 0.008–0.06 | 0.03 | 0.06 |
| | Trovafloxacin | | 0.015–0.25 | 0.03 | 0.06 |
| | Sparfloxacin | | 0.015–0.25 | 0.03 | 0.06 |
| | Clinafloxacin | | not determined | | |
| Legionella spp. | 11 | 1 | 0.12–0.25 | 0.12 | 0.25 |
| | | 3 | 0.5–1 | 0.5 | 1 |
| | | 4 | 0.25–0.5 | 0.25 | 0.25 |
| | | 5 | 0.12–0.25 | 0.25 | 0.25 |
| | Ciprofloxacin | | 0.12–0.5 | 0.25 | 0.5 |
| | Trovafloxacin | | 0.12–0.25 | 0.12 | 0.25 |
| | Sparfloxacin | | 0.03–0.25 | 0.06 | 0.25 |
| | Clinafloxacin | | 0.03–0.12 | 0.06 | 0.12 |
| M. pneumoniae | 7 | 1 | 0.015–0.03 | | |
| | | 3 | 0.06–0.12 | | |
| | | 4 | 0.015–0.03 | | |
| | | 5 | 0.015–0.03 | | |
| | Ciprofloxacin | | 1–2 | | |
| | Trovafloxacin | | 0.12–0.25 | | |
| | Sparfloxacin | | 0.06–0.12 | | |
| | Clinafloxacin | | 0.015–0.03 | | |
| N. gonorrhoeae | 12 | 1 | 0.001–0.015 | 0.002 | 0.004 |
| | | 3 | 0.008–0.06 | 0.008 | 0.03 |
| | | 4 | 0.002–0.015 | 0.002 | 0.015 |
| | | 5 | 0.002–0.015 | 0.002 | 0.015 |
| | Ciprofloxacin | | 0.004–0.12 | 0.008 | 0.03 |
| | Trovafloxacin | | 0.015–0.12 | 0.015 | 0.06 |
| | Sparfloxacin | | £0.002–0.06 | 0.004 | 0.015 |
| | Clinafloxacin | | 0.004–0.015 | 0.004 | 0.015 |
| H. pylori | 17 | 1 | 0.008–0.03 | 0.03 | 0.03 |
| | | 3 | 0.06–0.5 | 0.12 | 0.25 |
| | | 4 | 0.06–0.25 | 0.12 | 0.25 |
| | | 5 | 0.015–0.06 | 0.03 | 0.06 |
| | Ciprofloxacin | | 0.12–0.5 | 0.5 | 0.5 |
| | Trovafloxacin | | 0.06–1 | 0.12 | 0.5 |
| | Sparfloxacin | | 0.06–0.25 | 0.12 | 0.25 |
| | Clinafloxacin | | 0.008–0.03 | 0.015 | 0.03 |
| M. avium | 20 | 1 | 0.25–8 | 1 | 4 |
| | | 3 | 1–32 | 4 | 16 |
| | | 4 | 0.25–4 | 0.25 | 1 |
| | | 5 | 0.25–4 | 1 | 2 |
| | Ciprofloxacin | | 4→128 | 16 | 32 |
| | Trovafloxacin | | 8–128 | 32 | 64 |
| | Sparfloxacin | | £0.5–16 | 2 | 2 |
| | Clinafloxacin | | 2→128 | 16 | 32 |

As can be seen from Table 1, the in vitro activity of the compound of the invention in Example 1 was found to be superior to ciprofloxacin, sparfloxacin, and trovafloxacin, against staphylococci, streptococci, and enterococci with $MIC_{90}$'s of 0.03 (g/ml, 0.06 (g/mL, and 0.25 to 1 (g/mL, respectively. The activity of the compound of Example 1 was equivalent to ciprofloxacin and superior to trovafloxacin and sparfloxacin against the enterobacteriaceae; the $MIC_{90}$'s ranged from 0.015 to 0.25 (g/mL against isolates from eight genera. The compound was significantly more active than ciprofloxacin, trovafloxacin, and sparfloxacin against the anaerobes with $MIC_{90}$'s against *B.fragilis, C. difficile, and C. perfringens* of 0.12 (g/mL, 0.5 9g/mL, and 0.12 (g/mL, respectively. Moreover, Example 1 was highly active against ciprofloxacin resistant strains: the $MIC_{90}$ for Example 1 was 0.5 (g/mL for staphylococcal strains with a ciprofloxacin $MIC_{90}$ of >128 (g/ml, while the $MIC_{90}$ for 1.1 was 16 (g/mL for *P. aeruginosa* strains with a ciprofloxacin $MIC_{90}$ of 128 (g/mL. Thus, compound of the invention, demonstrates excellent, broad-spectrum antibacterial activity.

Antibacterial Activity (in vivo Efficacy Data)

For the efficacy evaluation, female CF-1 outbred mice (Charles Rivers Laboratories) of approximately 8 weeks of age and 25 gram body mass were inoculated intraperitoneally with overnight cultures of *staphylococcus aureus* NTCC 10649, *Streptococcus pneumoniae* 6303, *Escherichia coli* JUHL. The inoculums were adjusted to yield approximately $100 \times LD_{50}$ or log 6.6 for *S. aureus*, log 3.0 for *S. pneumoniae*, and log 6.3 for *E. coli*.. Test compounds were formulated in sterile water for injection and were administered by the subcutaneous (SC) or oral (PO) route at one and five hours post infection. Concurrently with each trial, the challenge $LD_{50}$ was validated by inoculation of untreated mice with log dilutions of the bacterial inoculum. A five log dilution range of the bacterial challenges was inoculated into five groups of ten mice each (ten mice per log dilution). A mortality rate of 100% was produced in all groups of untreated mice at the 100 ×$LD_{50}$ challenge inoculum. Mice were monitored daily for mortality for seven days. The mean effective dose to protect 50% of the mice ($ED_{50}$) was calculated from cumulative mortality by logarithmic-probit analysis of a plotted curve of survival versus dosage as described in *Antimicrob. Agents Chemother.* 31: 1768–1774 and *Proc. Soc. Exp. Biol. Med.* 1994, 57, 261–264, each of which are hereby incorporated by reference. There were ten mice per dosage group.

TABLE 2

$ED_{50}$ values (mg/kg/day) in mice by subcutaneous or oral route

| Example | S. aureus | | S. pneumoniae | | E. coli | |
|---|---|---|---|---|---|---|
| | SC | PO | SC | PO | SC | PO |
| 1 | 1.5 | 5.0 | 12.5 | 20.0 | 1.4 | 6.8 |
| 2 | 0.6 | 3.4 | 1.6 | 5.3 | 0.1 | 0.6 |
| 5 | 0.9 | 2.3 | 0.9 | 4.2 | 0.6 | 5.0 |
| ciprofloxacin | 3.1 | 18.3 | >50 | >100 | 1.0 | 4.1 |

Thus, example 1 demonstrated broad spectrum efficacy against both gram positive and gram negative infections. Oral efficacy was also demonstrated against all infections. 1 was superior to ciprofloxacin against *S. aureus, S. pneumoniae*, and was comparable against *E. coli*.

Toxicity Data

For the toxicity evaluation, female outbred CF- 1 mice, approximately 8 weeks old and 25 gram body mass, received a single intraperitoneal injection (0.5 mL) of vehicle, Example 1, Example 2 or Example 3 on study day 0. The compounds were formulated in sterile water. Dose groups were: 25, 100, 200 and 400 mg/kg. Mice were monitored for clinical signs daily for 21 days. Body weights were determined weekly. Mortality was monitored for determination of $LD_{50}$, defined as the intraperitoneal dose which would be lethal to 50% of treated mice. The $LD_{50}$ values were calculated by linear regression using trimmed logit analysis (Hardy et al. and Miller et al.)

TABLE 3

In vivo Toxicity Data

| Example 1 | (mg/kg) | % wt $D^2$ | $LD_{50}$ (# alive/5) | $MST^3$ (days) |
|---|---|---|---|---|
| 1 | 400 | | 232.2 | |
| | 200 | NA | 0/5 | 0.0 |
| | 100 | 10.0 | 4/5 | 11.0 |
| | 25 | 20.6 | 5/5 | NA |
| | | 18.4 | 5/5 | NA |
| 2 | 400 | | 38.8 | |
| | 200 | NA | 0/5 | 0.0 |
| | 100 | NA | 0/5 | 0.0 |

TABLE 3-continued

In vivo Toxicity Data

| Example 1 | (mg/kg) | % wt $D^2$ | $LD_{50}$ (# alive/5) | $MST^3$ (days) |
|---|---|---|---|---|
| | 25 | −38.1 | 0/5 | 7.6 |
| | | 10.4 | 5/5 | NA |
| 5 | 200 | | 105.0 | |
| | 100 | NA | 0/5 | 5.2 |
| | 25 | −18.1 | 3/5 | 13.0 |
| | | 8.5 | 5/5 | NA |
| Control[1] | | 13.9 | 4/4 | NA |

[1]Control group received water vehicle.
[2]Per cent weight change as compared to weight on day 0.
[3]Mean survival time.
NA = not applicable.

Example 1 was significantly less toxic than Example 2 or Example 5 when administered as a single intraperitoneal injection to mice. The 100 mg/kg dose of Example 5 and Example 2 produced 18% and 38% body weight loss, respectively. In contrast, no weight loss was observed for the 100 mg/kg dose of 1. The $LD_{50}$ for Example 1 was 232.2 mg/kg compared to 105.0 mg/kg for Example 3 and 38.8 mg/kg for Example 2. These findings demonstrate that Example 1, the compound of the invention, produces less morbidity and mortality than equivalent doses of Example 2 and Example 5.

Considering the toxicity data generated, Example 1 demonstrated approximately sixfold less toxicity ($LD_{50}$ values 232.2 mg/kg vs 38.8 mg/kg) than Example 2 while maintaining efficacy versus *S. aureus. S. pneumoniae* and *E. coli*.. Example 1 showed approximately two fold less toxicity than Example 5 ($LD_{50}$ values 232.2 mg/kg versus 105.0 mg/kg) while maintaining efficacy. The potential improvement in safety margin demonstrated by Example 1 compared to Example 2 and Example 5 in mice was marked.

We claim:
1. A compound represented by the formula:

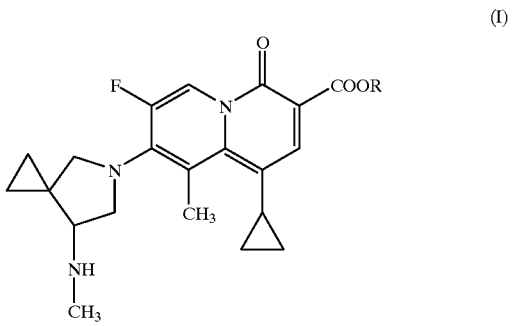

(I)

wherein R is selected from the group consisting of hydrogen, loweralkyl, and a pharmaceutically acceptable cation.

2. The compound according to claim 1 represented by the formula:

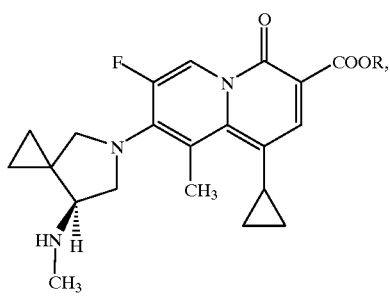

(II)

wherein R is as defined in claim 1.

3. A pharmaceutical composition comprising a compound according to claim 1 in combination with a pharmaceutically acceptable carrier.

4. A method of treating a bacterial infection in a human or veterinary patient, comprising administering to the patient a therapeutically effective amount of a compound according to claim 1.

5. A pharmaceutical composition comprising a compound according to claim 2 in combination with a pharmaceutically acceptable carrier.

6. A method of treating a bacterial infection in a human or veterinary patient, comprising administering to the patient a therapeutically effective amount of a compound according to claim 2.

* * * * *